United States Patent
Suzuki et al.

(10) Patent No.: US 6,787,546 B2
(45) Date of Patent: Sep. 7, 2004

(54) HETEROCYCLE DERIVATIVES AND DRUGS

(75) Inventors: Toshiyuki Suzuki, Saitama (JP); Tomiyoshi Aoki, Shiga (JP)

(73) Assignee: Nippon Shinyaku Co., Ltd. (JP)

( * ) Notice: Subject to any disclaimer, the term of this patent is extended or adjusted under 35 U.S.C. 154(b) by 129 days.

(21) Appl. No.: 10/149,622

(22) PCT Filed: Dec. 13, 2000

(86) PCT No.: PCT/JP00/08781

§ 371 (c)(1),
(2), (4) Date: Jun. 12, 2002

(87) PCT Pub. No.: WO01/44195

PCT Pub. Date: Jun. 21, 2001

(65) Prior Publication Data

US 2003/0022884 A1 Jan. 30, 2003

(30) Foreign Application Priority Data

Dec. 14, 1999 (JP) .............................................. 11-354101
Jul. 4, 2000 (JP) ........................................ 2000-202393

(51) Int. Cl.[7] ..................... A61K 31/44; A61K 31/444; C07D 213/38; C07D 213/89; C07D 401/12
(52) U.S. Cl. .............. 514/247; 512/252.02; 512/252.03; 512/252.11; 512/255.05; 512/255.06; 512/257; 544/224; 544/238; 544/295; 544/296; 544/333; 544/357; 544/405; 544/406; 546/262; 546/264; 546/334
(58) Field of Search .................... 544/224, 238, 544/295, 296, 333, 357, 405, 406; 546/262, 264, 334; 514/247, 252.02, 252.03, 252.11, 255.05, 255.06, 257

(56) References Cited

U.S. PATENT DOCUMENTS 5,529,999 A * 6/1996 Ray et al. .................... 514/249
5,721,246 A * 2/1998 Yoshino et al. ............. 514/300
5,972,976 A * 10/1999 Hidaka et al. .............. 514/357

FOREIGN PATENT DOCUMENTS

WO WO 95/2727699 * 10/1995
WO WO 2000/64875 * 11/2000

* cited by examiner

Primary Examiner—Richard L. Raymond
(74) Attorney, Agent, or Firm—Greenberg Traurig LLP; Eugene C. Rzucidlo

(57) ABSTRACT

The object of the invention is to provide an excellent compound as a drug.

The invention relates to a heterocyclic compound shown by the following formula:

$$A—B—D—E \quad [1]$$

wherein
A is heteroaryl or its oxide;
B is ethenylene;
D is optionally substituted phenylene; and
E is a group of the formula:

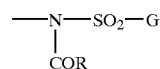

wherein G is optionally substituted phenyl;
and R is heteroaryl or heteroarylmethyl, or a group of the formula:

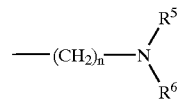

wherein n is an integer of 1 to 5; $R^5$ and $R^6$ are same or different and are independently selected from the group consisting of hydrogen, $C_1$—$C_6$ alkyl, hydroxyalkyl, aminoalkyl; or $R^5$ and $R^6$ taken together with the adjacent nitrogen atom may form 5- to 7-membered cyclic amino group for —$NR^5R^6$ or a salt thereof.

11 Claims, No Drawings

HETEROCYCLE DERIVATIVES AND DRUGS

TECHNICAL FIELD

The present invention relates to novel heterocyclic compounds or salts thereof, which are useful as a medicine.

BACKGROUND ART

Heterocyclic compounds of the formula below have been known to be useful as anticancer agent (WO95/027699).

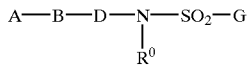

wherein A is optionally substituted heteroaryl or its oxide, B is optionally substituted ethenylene, D is optionally substituted phenylene, G is optionally substituted phenyl and $R^0$ is hydrogen, acetyl, optionally substituted alkyl or optionally substituted alkenyl.

It has also been known that (E)-4-(2-(2-(N-(4-methoxy-benzenesulfonyl) amino)phenyl)ethenyl)pyridine 1-oxide (hereinafter, referred to as "Compound A") has a potent growth inhibition activity on cancer cells, and that (E)-4-(2-(2-(N-(4-acetyl-N-(4-methoxy-benzenesulfonyl)amino)phenyl)ethenyl)pyridine 1-oxide (hereinafter, referred to as "Compound B") has an anticancer activity with low toxicity. Accordingly, the Compounds A and B have been expected to be promising drugs for oral administration in the treatment of various malignant tumors such as lung cancer, breast cancer, gastrointestinal cancer, prostate cancer, blood cancer and the like.

Although Compounds A and B are suited for oral administration, they can hardly been used in a liquid form for intravenous injection or the like because of extremely low solubility in injectable solutions.

The absorptiveness of anticancer agents, when administered orally, sometimes varies depending on individuals; and hence intravenous administration is mainly employed for the treatment of cancer from the viewpoint of reliability, accuracy and safety. The intravenous injection is convenient when a patient is unable to accept the oral administration. Under the conditions, anticancer agents useful as an injection have been demanded in the field of clinical medicine.

DISCLOSURE OF THE INVENTION

The purpose of the present invention is to provide novel compounds having a potent anticancer activity which are water-soluble and injectable.

The present inventors have synthesized and investigated into various compounds, during which they found that compounds of the formula [I] below are water-soluble and have extremely high anticancer activity among them, and thus completed the present invention.

The present invention relates to the following (1)–(10).

(1) A compound of the formula [I] or a salt thereof:

A—B—D—E     [1]

wherein

A is optionally substituted heteroaryl or its oxide;

B is optionally substituted ethenylene;

D is optionally substituted phenylene; and

E is a group of the formula:

wherein G is optionally substituted phenyl; and R is optionally substituted heteroaryl or heteroarylmethyl, or a group of the formula:

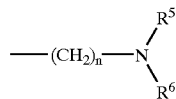

wherein n is an integer of 1 to 5; $R^5$ and $R^6$ are same or different and independently selected from the group consisting of hydrogen, $C_1$—$C_6$ alkyl, hydroxyalkyl, aminoalkyl; or $R^5$ and $R^6$ taken together with the adjacent nitrogen atom may form a 5- to 7-membered cyclic amino group for —$NR^5(R^6)$ which may optionally be substituted and, in addition to the nitrogen atom, may optionally comprise an oxygen, sulfur or nitrogen atom as a ring-composing member.

(2) The compound of the formula [I] mentioned in the above (1) or a salt thereof, wherein A is 4-pyridyl or 1-oxido-4-pyridyl; B is ethenylene; D is optionally substituted phenylene; and E is the group of the formula:

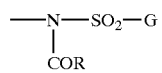

wherein R and G are the same as defined in claim 1.

(3) The compound of the formula [I] mentioned in the above (1) or a salt thereof, wherein A is 4-pyridyl or 1-oxido-4-pyridyl; B is ethenylene; D is optionally substituted phenylene; E is the group of the formula:

wherein G is optionally substituted phenyl and R is the group of the formula:

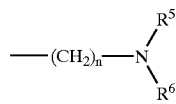

wherein n, $R^5$ and $R^6$ are the same as defined in claim 1.

(4) The compound mentioned in the above (3) or a salt thereof, wherein $R^5$ and $R^6$ are same or different and independently selected from the group consisting of hydrogen, $C_1$—$C_6$ alkyl; or $R^5$ and $R^6$ taken together with the adjacent nitrogen atom may form an optionally substituted 5- to 6-membered cyclic amino group for —$NR^5(R^6)$.

(5) The compound of the formula [I] mentioned in the above (1) or a salt thereof, wherein A is 4-pyridyl or 1-oxido-4-pyridyl; B is ethenylene; D is phenylene; and E is a group of the formula:

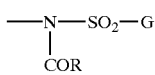

wherein G is optionally substituted phenyl; and R is optionally substituted 5- to 6-membered heteroaryl or heteroarylmethyl.

(6) The salt mentioned in the above (1), wherein the salt is hydrochloride.

(7) A pharmaceutical composition comprising a compound of the formula [1] in the above-mentioned (1) or a salt thereof as an active ingredient.

(8) The pharmaceutical composition of the above-mentioned (7) which is in a form of injection.

(9) An anticancer agent comprising a compound of the formula [I] in the above-mentioned (1) or a salt thereof as an active ingredient.

(10) The anticancer agent of the above-mentioned (9) which is in a form of injection.

The structural feature of the compound of the present invention is that phenyl in the stilbazole nucleus carries an aminoacylamino group, or a heteroaroylamino group or a heteroaroylaminomethyl group containing nitrogen atom.

The compound having the above structural feature is a novel compound never documented heretofore. The compound of the present invention has a superior anticancer activity with a low toxic potential.

The present invention will hereinafter be described in detail.

Terms herein used to show various substituents are defined below.

Examples of "phenylene" group include 1,2-phenylene, 1,3-phenylene and 1,4-phenylene. The phenylene group may have one or two substituents at an arbitrary position(s), examples of which include hydroxy, halogen, amino, $C_1$—$C_6$ alkyl and $C_1$—$C_6$ alkoxy. Among others, optionally substituted 1,2-phenylene, especially non-substituted 1,2-phenylene, is preferred.

The ethenylene group may have a substituent(s) at each carbon atom, examples of which include cyano, bromo and $C_1$—$C_6$ alkyl. Among others, optionally substituted ethenylene, especially non-substituted ethenylene, is preferred.

The term "heteroaryl" refers to a 5- to 6-membered heteroaryl group having one to two nitrogen atoms as the ring-composing member. The heteroaryl group optionally has one or two substituents at an arbitrary position(s), examples of which include halogen, $C_1$—$C_6$ alkyl, $C_1$—$C_6$ alkoxy, hydroxy and $C_1$—$C_6$ aminoalkyl. The heteroaryl for A includes 6-membered heteroaryl, for example, 2-pyridyl, 3-pyridyl, 4-pyridyl, 2-pyrimidinyl, 4-pyrimidinyl, 5-pyrimidinyl, 3-pyridazinyl, 4-pyridazinyl and pyrazinyl. Among others, non-substituted 4-pyridyl is preferred. The heteroaryl for R includes a 5- to 6-membered one, for example, 2-pyridyl, 3-pyridyl, 4-pyridyl, 2-pyrimidinyl, 4-pyrimidinyl, 5-pyrimidinyl, 3-pyridazinyl, 4-pyridazinyl, 1-imidazolyl, 2-imidazolyl and 4-imidazolyl.

The term "alkyl" refers to a straight or branched alkyl group of 1-6 carbons, and includes, for example, methyl, ethyl, n-propyl, isopropyl, n-butyl, isobutyl, sec-butyl, tert-butyl, n-pentyl, isopentyl, n-hexyl, isohexyl, and the like. Among others, $C_1$—$C_3$ alkyl, especially methyl is preferred.

The alkyl moiety of "hydroxyalkyl" and "aminoalkyl" is as defined above.

Examples of "cyclic amino" include, for example, pyrrolidin-1-yl, piperidino, hexamethylenimino, tetrahydropyridin-1-yl, octahydroazosin-1-yl, piperazin-1-yl, homopiperazin-1-yl, morpholino and thiomorpholino. The cyclic amino may have one or two substituents selected from the group consisting of alkyl, alkenyl, alkynyl, aryl, aralkyl and a heterocyclic group having a nitrogen atom, at any position. Among others, non-substituted pyrrolidin-1-yl, piperidino, morpholino as well as piperazin-1-yl substituted with pyridyl are preferred.

Examples of "halogen" include fluorine, chlorine, bromine, iodine and the like.

The "phenyl" group may have one or two substituents, for example, hydroxy or $C_1$—$C_6$ alkoxy. Among others, phenyl substituted with alkoxy, especially 4-methoxyphenyl, is preferred. The alkylene represented by "—$(CH_2)_n$—" may have a substituent selected from the group consisting of amino or $C_1$—$C_6$ alkyl at any position.

The term "alkoxy" refers to a straight or branched alkoxy group of 1-6 carbons, and includes, for example, methoxy, ethoxy, n-propoxy, isopropoxy, n-butoxy, isobutoxy, sec-butoxy, tert-butoxy, n-pentyloxy, isopentyloxy, n-hexyloxy, isohexyloxy, and the like. Among others, $C_1$—$C_3$ alkoxy, especially methoxy, is preferred.

The term "alkenyl" refers to a straight or branched alkenyl group of 2-6 carbons, and includes, for example, vinyl, 1-propenyl, 2-propenyl, isopropenyl, 2-butenyl, 3-butenyl, isobutenyl, methalyl, prenyl, isoprenyl, 1,1-dimethylallyl, and the like. $C_2$—$C_4$ alkenyl is especially preferred.

The term "alkynyl" refers to a straight or branched alkynyl group of 2–6 carbons, and includes, for example, ethynyl, 1-propynyl, 2-propynyl, 2-butynyl, 3-butynyl, 3-methyl-2-butynyl, and the like. $C_2$—$C_4$ alkynyl is especially preferred.

The term "aryl" refers to an aryl of 6–10 carbons, for example, phenyl, 1-naphthyl and 2-naphthyl.

The term "aralkyl" refers to an aralkyl of 7–8 carbons, for example, benzyl and phenethyl.

The term "hetero ring having nitrogen atom" refers to the above-mentioned cyclic amino or heteroaryl. Such hetero ring may have one or two substituents selected from the group consisting of alkyl, amino, hydroxy and oxo.

The salts of a compound [1] which fall within the scope of the invention include pharmaceutically acceptable salts formed with inorganic acids such as hydrochloric acid, sulfuric acid, nitric acid, phosphoric acid, hydrofluoric acid and hydrobromic acid; organic acids such as acetic acid, tartaric acid, lactic acid, citric acid, fumaric acid, maleic acid, succinic acid, methanesulfonic acid, ethanesulfonic acid, benzenesulfonic acid, toluenesulfonic acid, naphthalenesulfonic acid and camphorsulfonic acid.

The compound of the present invention may exist in cis (Z) and trans (E) forms. The respective isomers and their mixtures also fall within the scope of the present invention. Among others, E-form is preferred.

Among the compound of the invention of the formula [I], compounds are preferred wherein A is optionally substituted pyridyl or 1-oxidopyridyl, especially non-substituted 4-pyridyl or 1-oxido-4-pyridyl; B is ethenylene with a trans-form, especially non-substituted ethenylene with a trans-form; D is non-substituted 1,2-phenylene; and E is 4-substituted phenyl with preference for 4-alkoxy phenyl, especially 4-alkoxy phenyl.

(E)-4-(2-(2-(N-(4-methoxybenzenesulfonyl)-N-piperidinoacetylamino)phenyl)ethenyl)pyridine 1-oxide hydrochloride (the compound of Example 5), (E)-4-(2-(2-(N-(N,N-dimethylglycyl)-N-(4-methoxybenzenesulfonyl) amino)phenyl)ethenyl)pyridine 1-oxide hydrochloride (the compound of Example 8), (E)-4-(2-(2-(N-(4- methoxybenzenesulfonyl)-N-(4-(2-pyridyl)piperazino) acetylamino)phenyl)ethenyl)pyridine 1-oxide dihydrochloride (the compound of Example 9), (E) -4-(2-(2-(N-(4-methoxybenzenesulfonyl)-N-morpholinoacetylamino) phenyl)ethenyl)pyridine 1-oxide hydrochloride (the compound of Example 13) and (E)-4-(2-(2-(N-(4-methoxybenzenesulfonyl)-N-pyrrolidinoacetylamino) phenyl)ethenyl)pyridine 1-oxide hydrochloride (the compound of Example 14) are preferred for the present invention.

The compound of the present invention can be synthesized according to the processes illustrated below.

PROCESS 1

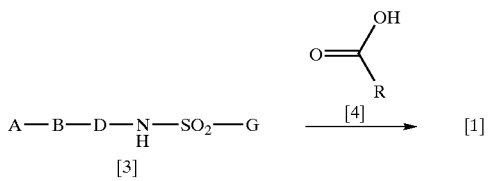

wherein A, B, D, G and R are as defined above.

A compound [3] and a carboxylic acid [4] are subjected to direct condensation reaction using a condensing agent according to the per se known method to give the compound [1]. The reaction can be carried out in the presence of a condensing agent such as N,N-dicyclohexylcarbodiimide (DCC), carbonyldiimidazole or diphenylphosphoryl azide (DPPA) in a suitable solvent (e.g., halogenated hydrocarbons such as methylene chloride and chloroform; ethers such as tetrahydrofuran and dioxane; acetonitrile; N,N-dimethylformamide (DMF), or the like), at about −30° C. to about 180° C. If necessary, 4-dimethylaminopyridine (DMAP) or 4-pyrrolidinopyridine (4-PPY) may be used as a catalyst. Based on 1 mole of the compound [3], from equimolar to a slightly excess amount of a compound [4] and a condensing agent (e.g., DCC) can be used. When a catalyst is used, the amount can be from 0.1 to 1 mole, based on 1 mole of the compound [3]. The reaction time depends on the kinds of the materials, the solvent, reaction temperature, or the like to be used in the reaction, but is normally from about 5 minutes to 70 hours.

Alternatively, the compound [1] can be prepared by reacting a compound [3] with a reactive derivative of a carboxylic acid [4] in an appropriate solvent. The reaction solvent may be any kind of solvent that does not interfere with the reaction, for example, ethers such as tetrahydrofuran, dioxane and diethyl ether; hydrocarbons such as benzene and toluene; halogenated hydrocarbons such as methylene chloride and chloroform; ketones such as acetone and methyl ethyl ketone; aprotic solvents such as N,N-dimethylformamide (DMF), N,N-dimethyl acetamide, pyridine or acetonitrile, or various mixtures of such solvents. The reactive derivative of a carboxylic acid includes those which are conventionally used such as acyl halides, carboxylic anhydrides, activated amides and activated esters. Above all else, the acyl halides are preferred. Such acyl halides include acyl chlorides and acyl bromides. The acid anhydrides include the mixed anhydrides prepared from monoalkylcarbonic acids and mixed anhydrides prepared from aliphatic carboxylic acids (e.g. acetic acid, pivalic acid, valeric acid, isovaleric acid, trifluoroacetic acid, etc.), and the symmetric anhydrides. The activated amides include such acid amides as imidazole, pyrazole, 4-substituted imidazole, dimethylpyrazole, triazole, tetrazole, and benzothiazole. The activated esters include such esters as the methyl ester, methoxymethyl ester, propargyl ester, 4-nitrophenyl ester, 2,4-dinitrophenyl ester, trichlorophenyl ester, methanesulfonyl ester, N-hydroxysuccinimide and N-hydroxyphthalimide.

When an acyl halide is used in the present process, the reaction is preferably conducted in the presence of a suitable base. Examples of such a base include alkali metal compounds such as potassium carbonate, sodium hydroxide, potassium hydroxide, sodium hydride and sodium methylate, and organic tertiary amines such as pyridine, triethylamine and triethylenediamine. The reaction can proceed at room temperature in many instances; but it can be carried out under cooling or heating at temperature range of between −78° C. and 150° C., preferably 0° C. and 120° C., when necessary. The proportion of the compound [4] based on the compound [3] is preferably 1 through 10 molar equivalents and more preferably 1 through 3 molar equivalents. The reaction time depends on the starting compounds, solvent, reaction temperature, and the like, to be employed, but is normally from about 5 minutes to 70 hours. The compound [1] can be also prepared by Mitsunobu reaction (see, Synthesis 981, 1).

Process 2

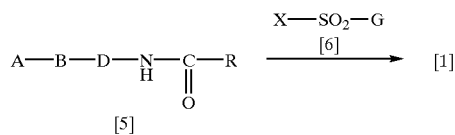

wherein A, B, D, R and G are as defined above and X is halogen,

The compound [1] of the present invention can be prepared by reacting a compound [5] with a compound [6] in an appropriate solvent. The reaction can be carried out substantially in the same procedure as that used for the reaction between a reactive derivative of carboxylic acid and a compound [3] in Process 1 above.

The resulting compound [1] thus produced can be isolated and purified by the per se known procedures such as concentration, pH adjustment, redistribution, solvent extraction, crystallization, recrystallization, fractional distillation, and chromatography.

The starting compound [3] can be prepared in accordance with a known process (WO95/27699).

The starting compound of the formula [4] wherein R is —(CH$_2$)$_n$—NR$^5$R$^6$ (compound [4a]), among others, can be prepared according to the reaction scheme below as hereinafter described in the Reference Example.

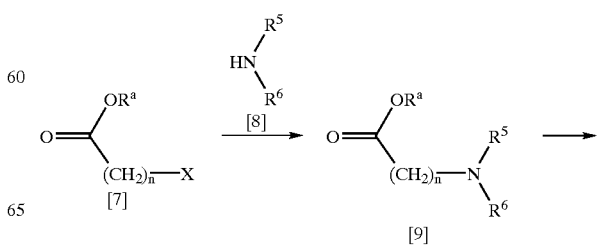

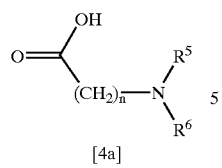

[4a]

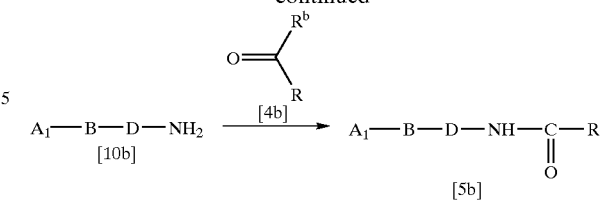

wherein $R^5$, $R^6$, n and X are as defined above and $R^a$ is a protecting group for a hydroxy group.

As for the starting compounds of the formula [4] wherein R is heteroaryl or heteroarylmethyl, among others, can be commercially available heteroaryl carboxylic acids or heteroaryl acetic acids, or derivatives thereof, or those which can be produced from the existing ones according to a per se known procedure.

The starting compounds [5] can be prepared according to the following reaction scheme.

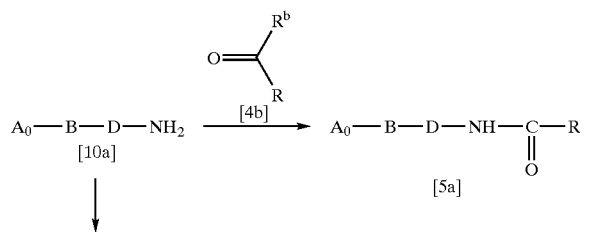

wherein B, D and R are as defined above; $A_0$ is heteroaryl corresponding to A; $A_1$ is oxide of $A_0$; and $R^b$ is a leaving group.

Examples of the leaving group include chloro, bromo, iodo, hydroxy group, alkoxycarbonyloxy group, and the like.

The compound [10a] is reacted with the compound [4b] in an appropriate solvent to obtain the compound [5a] corresponding to a compound of the formula [5] wherein A is heteroaryl. The reaction can be carried out substantially in accordance with the method used in Process 1 above. The compound [10a] may be converted into the oxide [10b] by reacting with an organic peroxide in accordance with a procedure known in a text (Jikken Kagaku Koza 21, Yukikagobutsu-no-Gosei III (Part 2), p. 295, 1958) before subjecting to the reaction with the compound [4b], which gives the compound [5b] corresponding to a compound of the formula [5] wherein A is the oxide of heteroaryl.

The compounds wherein R is —$(CH_2)_n$—$NR^5R^6$ can also be prepared according to the following reaction scheme.

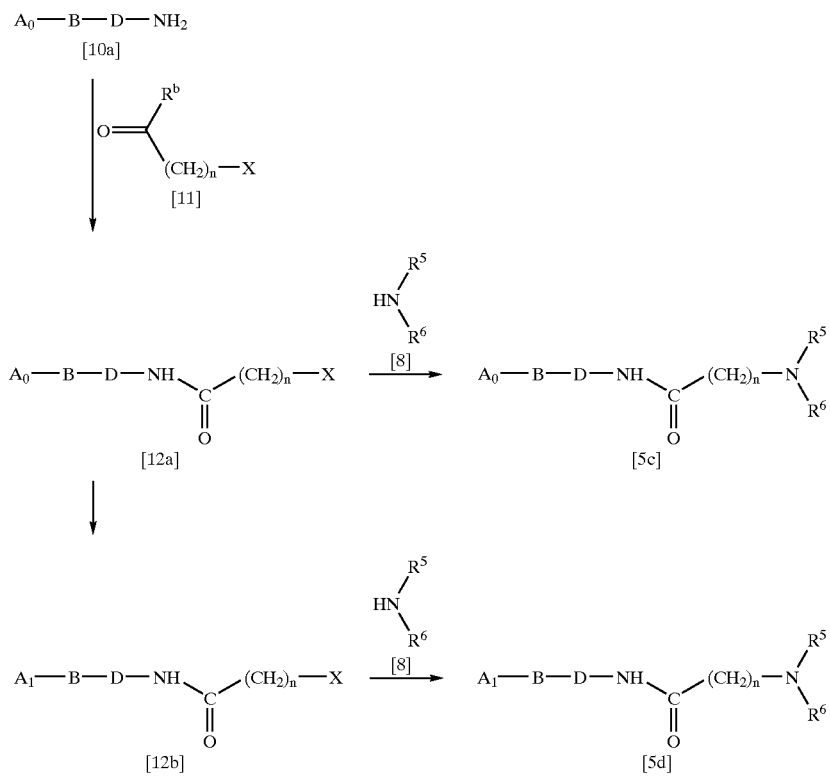

wherein $A_0$, $A_1$, B, D, $R^5$, $R^6$, n, X and $R^b$ are as defined above.

The compound [12a] can be prepared by reacting the compound [10a] with the compound [11] in an appropriate solvent in the same manner as Process 1; however, when the compound [11] is a reactive derivative of carboxylic acid, a base is needed. The compound [12a] is reacted with the amine [8] in an appropriate solvent optionally in the presence of a base at 0° C. to 160° C., preferably, at 10° C. to 120° C. to yield the compound [5c] corresponding a compound of the formula [5] wherein R is —$(CH_2)_n$—$NR^5R^6$ and A is heteroaryl. If desired, the compound [12a] can be reacted with an organic peroxide by a method described in a text (Jikken Kagaku Koza 21, Yukikagobutsu-no-Gosei, III, Part 2, p. 295, 1958) to give the oxide [12b], which in turn reacted with the compound [8] by the same procedure as that used for the reaction between the compound [8] and the compound [12a] to give the compound [5d] corresponding to a compound of the formula [5] wherein R is —$(CH_2)_n$—$NR^5R^6$ and A is the oxide of heteroaryl.

The compound [5d] can also be prepared according to the following reaction scheme.

tection can be effected at an appropriate stage by the per se known method such as acid treatment, alkaline treatment or catalytic reduction.

Examples of amino-protecting groups include benzyl, benzyloxycarbonyl and trifluoroacetyl. Examples of hydroxy-protecting group include methoxymethyl, 2-methoxyethoxymethyl, methylthiomethyl, tetrahydropyranyl, tert-butyl, benzyl, trimethylsilyl and tert-butyldimethylsilyl.

The salts of the compounds [1] of the present invention can be produced by the per se known method. For example, a hydrochloride of the compounds [1] of the present invention can be prepared by treating a compound [1] with a solution of hydrogen chloride in alcohol or ethyl ether and recovering the crystalline precipitates by filtration. In case that there are no/little crystalline precipitates, the solution can be concentrated and the deposited crystals are filtered off.

When the compound of the invention is administered as a medicine, it can be administered to mammals inclusive of humans as it is or as a pharmaceutical composition containing the compound in a pharmaceutically acceptable, non-

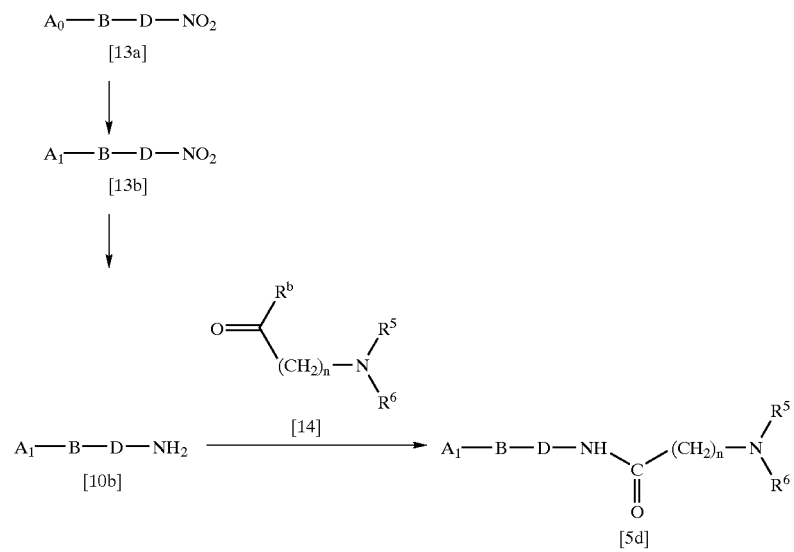

wherein $A_0$, $A_1$, B, D, $R^5$, $R^6$, n, and $R^b$ are as defined above.

The compound [13a] is converted into the compound [13b] by the same procedure as that used for the conversion of the compound [12a] into the compound [12b]. The compound [13b] is then reduced according to a method known in a text (Shin-Jikken Kagaku Koza 14, Yukikagobutsu-no-Gosei, Part 3, p. 1333, 1978) to yield the compound [10b]. The compound [10b] and the compound [14] are reacted by the same procedure as the reaction between the compound [10b] and the compound [4b] to yield the compound [5d].

The starting compounds [4b] and [11] are either commercially available or prepared in the same manner as Reference Example.

The starting compounds [6], [7] and [8] are commercially available.

The starting compound [10a] can be prepared according to the method described in WO95/27699.

In the processes above, an amino or hydroxy group may be optionally protected with a conventional protecting group before subjecting the compounds to the reaction. The deprotoxic and inert carrier at a concentration of, for example, 0.1% to 99.5%, preferably 0.5% to 90%.

Examples of carrier usable include solid, semisolid, or liquid diluents, fillers, and other formulation auxiliaries, and at least one of them is employed. The pharmaceutical composition is preferably administered in a unit dosage form. The compound of the present invention is water-soluble, and can be used in the form of solutions (e.g., injection for intravenous or intracystic administration or syrup for oral administration), as well as in the solid form. The pharmaceutical composition of the present invention can be administered into tissues (hereinafter, referred to as "parenteral administration"), orally, locally (e.g. transdermally) or rectally. A dosage form suited for each administration mode is of course employed. For instance, the intravenous administration is especially preferred.

The dosage of the compound as an anticancer drug should preferably be adjusted in consideration of conditions of the patient such as age, body weight, nature and severity of disease, as well as the route of administration; but the daily dosage of the compound of the present invention as an active ingredient for adult for intravenous administration can generally be 0.1 mg -1,000 mg, preferably 1 mg -500 mg. The dose range above is not critical and a lower dosage may be sufficient in some cases, while a higher dosage beyond the said range may be needed in other cases. The daily dosage is preferably administered in one time, in general. The composition of the present invention can be also administered continuously or intermittently.

Parenteral administration can be carried out using a liquid unit dosage form, such as a solution, for subcutaneous, intramuscular or intravenous administration. Such a dosage form can be prepared by dissolving a predetermined amount of the compound in a nontoxic liquid vehicle for injection, such as an aqueous or oily vehicle, and sterilizing the solution. Alternatively, it can be prepared by dispensing a predetermined amount of the compound in each vial, sterilizing the vial and contents, and sealing the vial. For extemporaneous dissolution or blending, a powdery or lyophilized active compound may be accompanied by a spare vial and a vehicle. To isotonize an injection, a nontoxic salt or salt solution can be added. In addition, stabilizers, preservatives, emulsifiers, and other additives may also be concomitantly used.

Oral administration can be carried out using a solid or liquid unit dosage form, such as bulk powders, powders, tablets, dragees, capsules, granules, suspensions, solutions, syrups, drops, sublingual tablets, suppository and other forms. Bulk powders are prepared by comminuting the active substance to a suitable particle size. Powders are prepared by comminuting the active substance to a suitable size and blending the resulting powder with similarly comminuted pharmaceutical carriers such as edible carbohydrates, e.g. starch, mannitol, etc., and other substances, if any. Where necessary, flavorants, preservatives, dispersing agents, colorants, perfumes, etc. can be added.

Capsules are manufactured by encapsulating comminuted bulk particles, powders, or granules obtained in the manner described below for tablets in gelatin or other capsule shells. A lubricant or fluidizing agent, e.g. colloidal silica, talc, magnesium stearate, calcium stearate, solid polyethylene glycol, etc., can be added to the powdery materials prior to encapsulation. The medicinal efficacy of a capsule after ingestion may be improved by adding a disintegrator or a solubilizer, e.g. carboxymethylcellulose, carboxymethylcellulose calcium, low-substitution-degree hydroxypropylcellulose, croscarmellose sodium, carboxystarch sodium, calcium carbonate, and sodium carbonate.

The finely pulverized powder may be suspended and dispersed in vegetable oil, polyethylene glycol, glycerin or a surfactant and packaged in gelatin sheet to provide soft capsules. Tablets can be manufactured by preparing a powdery composition, granulating or slugging it, adding a disintegrator or a lubricant thereto, and compressing the mixture. The powdery composition can be prepared by mixing a properly comminuted substance with a diluent or a base mentioned above, which may further contain, where necessary, a binder (e.g. carboxymethylcellulose sodium, hydroxypropylcellulose, methylcellulose, hydroxypropylmethylcellulose, gelatin, polyvinylpyrrolidone, polyvinyl alcohol, etc.), a dissolution retardant (e.g. paraffin, wax, hydrogenated castor oil, etc.), a reabsorption promoter (e.g. quartenary salts), and an adsorbent (e.g. bentonite, kaolin, dicalcium phosphate, etc.). The powdery composition can be granulated by wetting the material with a binder, e.g. a syrup, a starch paste, a solution of gum arabic or cellulose, or a polymer solution and, then, passing the wet mass through a sieve by force. The powder, without being granulated, can be compressed with a tablet machine to give slugs of crude form, which is then crushed to give granules.

The granules thus obtained can be protected against inter-adhesion by adding a lubricant such as stearic acid, a salt of stearic acid, talc or mineral oil. The lubricated granules are then compressed into tablets.

The resulting bare tablets can be film-coated or sugar-coated.

Without being subjected to the above granulation or slugging process, the drug may be directly compressed after mixing with a free-flowing inert carrier. A transparent or translucent protective coat comprising a hermetic shellac film, a sugar or polymer coat, or a wax glaze coat can also be applied.

Other oral dosage forms such as solutions, syrups and elixirs. can also be provided in unit dosage forms each containing a predetermined amount of the drug. A syrup can be manufactured by dissolving the compound in a suitable pleasantly flavored aqueous vehicle, while an elixir can be manufactured using a nontoxic alcoholic vehicle.

Where necessary, a unit dose formulation for oral administration may be microencapsulated. This formulation can also be coated with, or embedded in, a polymer, a wax, or the like to provide a prolonged action or sustained release of active ingredient.

Rectal administration can be carried out by using suppositories which can be manufactured by mixing the compound with a water-soluble or -insoluble low-melting solid base, such as polyethylene glycol, cacao butter, or a higher ester (e.g. myristyl palmitate), or a mixture of them.

Best Mode of Practicing the Invention

The following Examples for the preparation of starting compounds (Reference Examples) and the compounds of the present invention (Examples), as well as Formulation Examples and Test Examples are provided to further illustrate the present invention in more detail, which should not be interpreted in any way as to limit the scope thereof. The specific rotation was measured at 20° C.

REFERENCE EXAMPLE 1

Synthesis of 4-methylpiperazin-1-yl acetic acid

[Process 1]

Synthesis of benzyl 4-methylpiperazin-1-yl acetate

N-Methylpiperazine (2.29 g) was dissolved in DMF (20 ml). To the solution were added potassium carbonate (2.76 g) and benzyl bromoacetate (1.20 g) and the mixture was heated at 80° C. for 1 hour. The reaction mixture was concentrated under reduced pressure. The residue was combined with ice-water and extracted with chloroform. The extract was dried over magnesium sulfate and the solvent was distilled off under reduced pressure. The resulting residue was purified by silica gel column chromatography (eluent: $CH_2Cl_2/CH_3OH/NH_3$ (28% aq.)=90/10/1) to yield the objective compound (2.0 g, colorless oil).

The following compounds were prepared by the same procedure as described above.

Benzyl 4-piperidinopiperidinoacetate
Benzyl 4-(3-pyridyl)piperazin-1-yl acetate
Benzyl 4-(2-pyridyl)piperazin-1-yl acetate
Benzyl 4-pyrrolidinopiperidinoacetate
Benzyl piperidinoacetate
Ethyl 4-(4-piperidinopiperidino)butyrate
Ethyl 3-(4-piperidinopiperidino)propionate
Benzyl morpholinoacetate Benzyl pyrrolidinoacetate
Ethyl 2-piperidinopropionate
Process 2
Synthesis of 4-methylpiperazin-1-yl acetic acid
Benzyl 4-methylpiperazin-1-yl acetate (1.98 g) prepared in Process 1 above was dissolved in methanol (20 ml) and subjected to hydrogenolysis at room temperature under ordinary pressure for 4 hours in the presence of 10% palladium-carbon. The reaction solution was filtered and the filtrate was concentrated under reduced pressure to yield the objective compound (1.11 g, colorless crystals).
The following compounds were prepared by the same procedure as described above.

4-Piperidinopiperidinoacetic acid
4-(3-Pyridyl)piperazin-1-yl acetic acid
4-(2-Pyridyl)piperazin-1-yl acetic acid
4-Pyrrolidinopiperidinoacetic acid
Piperidinoacetic acid
Morpholinoacetic acid
Pyrrolidinoacetic acid

REFERENCE EXAMPLE 2

Synthesis of 4-(4-piperidinopiperidino)butyric acid hydrochloride

Ethyl 4-(4-piperidinopiperidino)butyrate (2.20 g) prepared in the same manner as Reference Example 1 (Process 1) was dissolved in ethanol (20 ml). After adding 1 N aqueous sodium hydroxide solution (11.7 ml), the mixture was heated to reflux for 4 hours with stirring. The reaction mixture was concentrated to dry. The residue was precipitated by diluting with ethanol followed by addition of 1 N hydrochloric acid under ice-cooling. The crystalline precipitates were filtered off and used as a starting material without further purification.

The following compounds were prepared by the same procedure as described above.

3-(4-Piperidinopiperidino)propionic acid hydrochloride
3-Piperidinopropionic acid hydrochloride

EXAMPLE 1

(E)-4-(2-(2-(N-Glycyl-N-(4-methoxybenzenesulfonyl)amino)phenyl)-ethenyl) pyridine 1-oxide hydrochloride (E) -4-(2-(2-(N-(4-Methoxybenzenesulfonyl)amino)phenyl)ethenyl)-pyridine 1-oxide (1.15 g) was dissolved in methylene chloride (25 ml), and N-(t-butoxycarbonyl)glycine (1.31 g) and 4-pyrrolidinopyridine (44 mg) were added thereto. To the mixture was added dropwise N,N-dicyclohexylcarbodiimide (1.55 g) dissolved in methylene chloride (15 ml), and the mixture was stirred over night at room temperature. The reaction solution was filtered and the filtrate was concentrated. The resultant residue was dissolved in ethyl acetate and washed with water. The organic layer was dried over magnesium sulfate and the solvent was distilled off under reduced pressure. The residue was purified by silica gel column chromatography (eluent: $CHCl_3$/$CH_3OH$=30/1) to yield a colorless powdery compound (2.10 g). The resultant product was dissolved in ethanol (20 ml) and allowed to reflux overnight after the addition of 1 N hydrochloric acid (20 ml). The reaction solution was concentrated and the precipitated crystals were washed with warm mixture of chloroform and methanol to yield the objective compound (0.70 g, colorless powder). M.p. 235–237° C.
Elemental analysis for $C_{22}H_{21}N_3O_5S \cdot HCl \cdot 2.5H_2O$
Calcd. (%): C, 50.67; H, 4.64; N, 8.06
Found (%): C, 50.69; H, 4.62; N; 8.01

EXAMPLE 2

(E)-4-(2-(2-(N-(4-Methylpiperazin-1-yl)acetyl-N-(4-methoxy -benzenesulfonyl)amino)phenyl)ethenyl)pyridine 1-oxide hydrochloride (E) -4-(2-(2-(N-(4-Methoxybenzenesulfonyl)amino)phenyl)ethenyl) pyridine 1-oxide (0.96 g) was dissolved in methylene chloride (25 ml), and 4-methylpiperazin-1-yl acetic acid (0.99 g) prepared in Reference Example 1 and 4-pyrrolidinopyridine (37 mg) were added thereto. To the mixture was added dropwise N,N'-dicyclohexylcarbodiimide (1.29 g) dissolved in methylene chloride (13 ml), and the mixture was stirred over night at room temperature. The reaction solution was filtered and the filtrate was concentrated. The resultant residue was subjected to silica gel column chromatography (eluent: $CHCl_3$/$CH_3OH$=100/1 to 10/1) to obtain fractions. To each fraction was added hydrochloric acid-ether solution followed by concentration. The residue was diluted with water, filtered through membrane filter and lyophilized to yield the objective compound (1.25 g, colorless powder).
MS(m/e): 523(M+)
$^1$H-NMR (DMSO-$d_6$): δ:2.69(3H,s), 3.18–3.52(9H,m), 3.76(1H,d), 3.82(3H,d), 7.08–7.23(3H,m), 7.43–7.72(6H,m), 7.88–8.05(3H,m), 8.54(2H,d), 11.25(1H,br)

EXAMPLE 3

(E) -4-(2-(2-(N-(4-Piperidinopiperidino)acetyl-N-(4-methoxy-benzenesulfonyl)amino)phenyl)ethenyl)pyridine 1-oxide dihydrochloride 4-Piperidinopiperidino acetic acid (1.70 g) prepared in the same manner as Reference Example 1 was subjected to the reaction and post-treatment as described in Example 2 to yield the objective compound (1.28 g, pale yellow powder).
MS(m/e): 591(M$^+$)
Elemental analysis for $C_{32}H_{38}N_4O_5S \cdot 2HCl \cdot 8H_2O$
Calcd. (%): C, 47.58; H, 6.99; N, 6.94
Found (%): C, 46.95; H, 6.72; N, 6.80
$^1$H-NMR(DMSO-$d_6$): δ:1.38–2.21(12H,m), 2.86–3.36(8H,m), 3.80(3H,s), 3.89(1H,d), 6.99–7.12(3H,m), 7.35–7.69(6H,m), 7.93–8.04(3H,m), 8.38(2H,d), 10.45(1H,br), 11.15(1H,br)

EXAMPLE 4

(E) -4-(2-(2-(N-(4-Pyrrolidinopiperidino)acetyl-N-(4-methoxy -benzenesulfonyl)amino)phenyl)ethenyl)pyridine 1-oxide dihydrochloride 4-Pyrrolidinopiperidinoacetic acid (1.59 g) prepared in the same manner as Reference Example 1 was subjected to the reaction and post-treatment as described in Example 2 to yield the objective compound (0.50 g, pale yellow powder).
MS(m/e): 577(M$^+$)
Elemental analysis for $C_{31}H_{36}N_4O_5S \cdot 2HCl \cdot 7H_2O$
Calcd. (%): C, 48.00; H, 6.76; N, 7.22
Found (%): C, 47.87; H, 6.76; N, 7.10
$^1$H-NMR(DMSO-$d_6$): δ:1.91–2.17(7H,m), 3.00–3.89(14H,m), 4.24(1H,d), 6.97–7.14(3H,m), 7.32–7.69(6H,m), 7.90–8.05(3H,m), 8.38(2H,d), 10.25(1H,br), 10.60(1H,br)

EXAMPLE 5

(E)-4-(2-(2-(N-(4-Methoxybenzenesulfonyl)-N-piperidinoacetyl -amino)phenyl)ethenyl)pyridine 1-oxide hydrochloride Piperidinoacetic acid (0.89 g) prepared in the same manner as Reference Example 1 was subjected to the reaction and post-treatment as described in Example 2 to yield the objective compound (0.85 g, colorless powder).
MS(m/e): 508(M$^+$)
$^1$H-NMR(DMSO-$d_6$): δ:1.67(6H,br), 2.87(2H,br), 3.35 (2H,br), 3.62(3H,s), 3.73(1H,d), 4.19(1H,d), 7.06–7.14(3H,m), 7.41–7.71(6H,m), 7.90–8.07(3H,m), 8.48(2H,m), 9.99(1H,br)

EXAMPLE 6

(E)-4-(2-(2-(N-Isonicotinoyl-N-(4-methoxybenzenesulfonyl)-amino)phenyl)ethenyl)pyridine 1-oxide dihydrochloride Isonicotinic acid (0.20 g) was subjected to the reaction and post-treatment treatment as described in Example 2 to yield the objective compound (0.25 g, pale yellow powder). M.p. 198–200° C.

Elemental analysis for $C_{26}H_{21}N_3O_5S \cdot 2HCl \cdot 0.5H_2O$
Calcd. (%): C, 54.84; H, 4.24; N, 7.37
Found (%): C, 54.98; H, 4.41; N, 7.39

EXAMPLE 7

(E)-4-(2-(2-(N-Nicotinoyl-N-(4-methoxybenzenesulfonyl)-amino)phenyl)ethenyl)pyridine 1-oxide dihydrochloride Nicotinic acid (0.20 g) was subjected to the reaction and post-treatment as described in Example 2 to yield the objective compound (0.24 g, pale yellow powder). M.p. 187–189° C.

Elemental analysis for $C_{26}H_{21}N_3O_5S \cdot 2HCl$
Calcd. (%): C, 55.72; H, 4.14; N, 7.50
Found (%): C, 55.45; H, 4.30; N, 7.38

EXAMPLE 8

(E)-4-(2-(2-(N-(N,N-Dimethylglycyl)-N-(4-methoxybenzenesulfonyl)-amino)phenyl)ethenyl)pyridine 1-oxide hydrochloride N,N-dimethylglycine (0.65 g) was subjected to the reaction as described in Example 2. The reaction solution was filtered and the filtrate was concentrated. The residue was diluted with toluene and isopropyl ether and stirred. The precipitated crystals were filtered off, washed with water, dried, and recrystallized from acetonitrile. The resultant white crystals were suspended in water, followed by addition of 1 N aqueous hydrochloric acid solution and stirring. The mixture was filtered through membrane filter and lyophilized to yield the objective compound (0.62 g, colorless powder). M.p. 158–162° C.

MS(m/e):468(M⁺)
Elemental analysis for $C_{24}H_{25}N_3O_5S \cdot HCl \cdot 4H_2O$
Calcd. (%): C, 50.04; H, 5.95; N, 7.29
Found (%): C, 49.73; H, 5.67; N, 7.37
¹H-NMR(DMSO-d₆): δ:2.70(6H,s), 3.75–4.18(2H,m), 3.84(3H,s), 6.95–7.15(3H,m), 7.36–7.70(6H,m), 7.91–8.05 (3H,m), 8.26(2H,d), 9.87(1H,br)

EXAMPLE 9

(E)-4-(2-(2-(N-(4-Methoxybenzenesulfonyl)-N-(4-(2-pyridyl)piperazino)acetylamino)phenyl)ethenyl)pyridine 1-oxide dihydrochloride 4-(2-Pyridyl)piperazin-1-yl acetic acid (1.10 g) prepared in the same manner as Reference Example 1 was subjected to the reaction as described in Example 2. The reaction solution was post-treated in the same manner as Example 8 to yield the objective compound (0.67 g, colorless powder). M.p. 167° C. (decomp.)

MS(m/e):586(M⁺)
Elemental analysis for $C_{31}H_{31}N_5O_5S \cdot 2HCl \cdot 4H_2O$
Calcd. (%): C, 50.96; H, 5.66; N, 9.58
Found (%): C, 51.40; H, 6.00; N, 9.46
¹H-NMR(DMSO-d₆): δ:3.0–4.0(12H,m), 4.19(1H,d), 6.82–7.15(5H,m), 7.37–7.82(7H,m), 7.94(2H,d), 8.02–8.10 (2H,m), 8.33(2H,d)

EXAMPLE 10

(E)-4-(2-(2-(N-(4-(3-Pyridyl)piperazino)acetyl-N-(4-methoxy-benzenesulfonyl)amino)phenyl)ethenyl)pyridin 1-oxide dihydrochloride 4-(3-pyridyl)piperazin-1-yl acetic acid (1.39 g) prepared in the same manner as Reference Example 1 was subjected to the reaction and post-treatment as described in Example 2 to yield the objective compound (1.30 g, pale yellow powder). M.p. 167° C. (decomp.)

MS(m/e):586(M⁺)
Elemental analysis for $C_{31}H_{31}N_5O_5S \cdot 2HCl \cdot 4H_2O$
Calcd. (%): C, 50.96; H, 5.66; N, 9.58
Found (%): C, 51.31; H, 6.00; N, 9.40
¹H-NMR(DMSO-d₆): δ:3.0–4.0(12H,m), 4.22(1H,d), 6.98–7.14(3H,m), 7.36–7.69(6H,m), 7.80–8.08(5H,m), 8.23–8.50(4H,m)

EXAMPLE 11

(E)-4-(2-(2-(N-(3-(4-Piperidinopiperidino)propionyl)-N-(4-methoxy-benzenesulfonyl)amino)phenyl)ethenyl)pyridine 1-oxide dihydrochloride 3-(4-Piperidinopiperidino)propionic acid hydrochloride prepared in the same manner as Reference Example 2 and triethylamine were subjected to the reaction and post-treatment as described in Example 2 to yield the objective compound (0.13 g, pale yellow powder). MS(m/e):605(M⁺)

Elemental analysis for $C_{33}H_{40}N_4O_5S \cdot 2HCl \cdot 4H_2O$
Calcd. (%): C, 52.87; H, 6.72; N, 7.47
Found (%): C, 52.13; H, 7.24; N, 7.47
¹H-NMR(DMSO-d₆): δ:1.10–2.40(10H,m), 2.6–3.05(6H, m), 3.06–3.80(7H,m), 3.84(3H,S), 6.88–7.21(3H,m), 7.38–7.64(6H,m), 7.89–8.04(3H,m), 8.34(2H,d), 10.5(1H, br), 10.7(1H,br)

EXAMPLE 12

(E)-4-(2-(2-(N-(4-(4-Piperidinopiperidino)butyryl)-N-(4-methoxy-benzenesulfonyl)amino)phenyl)ethenyl)pyridine 1-oxide dihydrochloride 3-(4-Piperidinopiperidino)butyric acid hydrochloride prepared in the same manner as Reference Example 2 and triethylamine were subjected to the reaction and post-treatment as described in Example 2 to yield the objective compound (0.88 g, pale yellow powder).

MS(m/e): 619(M⁺)
Elemental analysis for $C_{34}H_{42}N_4O_5S \cdot 2HCl \cdot 8H_2O$
Calcd. (%): C, 48.86; H, 7.24; N, 6.70
Found (%): C, 48.54; H, 6.60; N, 6.61
¹H-NMR(DMSO-d₆): δ:1.64–2.26(15H,m), 2.85(6H,br), 3.30–3.63(4H,m), 3.83(3H,s), 7.05–7.13(3H,m), 7.36–7.61 (6H,m), 7.88–8.03(3H,m), 8.30(2H,d), 10.84(2H,br)

EXAMPLE 13

(E)-4-(2-(2-(N-(4-Methoxybenzenesulfonyl)-N-morpholinoacetyl-amino)phenyl)ethenyl)pyridine 1-oxide hydrochloride The title compound was prepared in the same manner as Example 2 using morpholinoacetic acid obtained in the same manner as Reference Example 1.

MS(m/e): 510(M⁺)
¹H-NMR(DMSO-d₆) δ:2.80–3.30(4H,m), 3.55–4.20(9H, m), 6.95(1H,d), 7.09–7.15(2H,m), 7.36–7.96(6H,m), 7.89–8.05(3H,m), 8.24(2H,d), 10.40(1H,br)

EXAMPLE 14

(E)-4-(2-(2-(N-(4-Methoxybenzenesulfonyl)-N-pyrrolidinoacetylamino)-phenyl)ethenyl)pyridine 1-oxide hydrochloride The title compound was prepared in the same manner as Example 2 using pyrrolidinoacetic acid obtained in the same manner as Reference Example 1.

MS(m/e): 494(M⁺)
¹H-NMR(DMSO-d₆) δ:1.65–2.00(4H,m), 2.80–3.10(2H, m), 3.20–3.60(2H,m), 3.80(3H,s), 3.84–3.93(1H,m), 4.19–4.28(1H,m), 7.04(1H,d), 7.10–7.16(2H,m), 7.34–7.69 (6H,m), 7.88–8.04(3H,m), 8.25(2H,d), 10.11(1H,br)

EXAMPLE 15
(E)-4-(2-(2-(N-(3-Pyridylacetyl)-N-(4-methoxybenzenesulfonyl)-amino)phenyl)ethenyl)pyridine 1-oxide hydrochloride 3-Pyridylacetic acid hydrochloride and triethylamine were subjected to the reaction and post-treatment as described in Example 2 to yield the objective compound (1.06 g).

MS(m/e): 502(M$^+$)
$^1$H-NMR(DMSO-d$_6$): δ:3.59(1H,d), 3.84(3H,s), 3.85(1H,d), 7.01(2H,d), 7.35–8.10(11H,m), 8.40(1H,d), 8.54(2H,d), 8.77(1H,s), 8.82(1H,d), 9.90(1H,br)

EXAMPLE 16
(E) -4-(2-(2-(N-(3-Morpholinopropionyl) -N-(4-methoxybenzenesulfonyl) -amino)phenyl)ethenyl)pyridine 1-oxide dihydrochloride 3-Morpholinopropionic acid hydrochloride prepared in the same manner as Reference Example 2 and triethylamine were subjected to the reaction and post-treatment as described in Example 2 to yield the objective compound (1.08 g).

MS(m/e): 524(M$^+$)
$^1$H-NMR(DMSO-d$_6$): δ:2.57–3.92(15H,m), 7.12(2H,d), 7.25(1H,d), 7.42–7.67(6H,m), 7.91(2H,d), 8.02(1H,d), 8.45(2H,d), 11.04(1H,br)

EXAMPLE 17
(Another Method for Preparation)
(E)-4-(2-(2-(N-Morpholinoacetyl-N-(4-methoxybenzenesulfonyl)-amino)phenyl)ethenyl)pyridine 1-oxide hydrochloride Morpholinoacetic acid (5.18 g) prepared in the same manner as Reference Example 1 was dissolved in methylene chloride (230 ml), and triethylamine (4.86 g) was added thereto. To the mixture was added dropwise ethyl chlorocarbonate (5.21 g) under ice-cooling, and the mixture was stirred for thirty minutes at room temperature. To the mixture was added (E)-4-(2-(2-(N-(4-methoxybenzenesulfonyl) amino)phenyl)ethenyl)pyridine 1-oxide (7.65 g) and the mixture was further stirred for three hours at room temperature. The reaction solution was washed with water, dried over magnesium sulfate and concentrated. The resultant residue was dissolved in acetonitrile. To the solutuion was added hydrochloric acid-methanol and the mixture was stirred over night at room temperature. The precipitated crystals were filtered off, washed with acetonitrile and further with ether and the crude crystals were obtained. The recrystallizaion from methanol yielded the objective compound (8.16 g).

EXAMPLE 18
(E)-4-(2-(2-(N-(N',N'-Dimethylaminopropionyl)-N-(4-methoxybenzenesulfonyl)amino)phenyl)ethenyl)pyridine 1-oxide hydrochloride N,N-dimethylaminopropionic acid hydrochloride and triethylamine was subjected to the reaction and post-treatment as described in Example 2 to yield the objective compound.

TEST EXAMPLE 1
Solubility in Water

The water solubility of the compound of the present invention was measured at 25° C. As the control compounds, (E)-4-(2-(2-(N-(4-methoxybenzenesulfonyl)amino)-phenyl) ethenyl)pyridine 1-oxide (Compound A) and (E)-4-(2-(2-(N-acetyl-N-(4-methoxy-benzenesulfonyl)amino)phenyl) ethenyl)pyridine 1-oxide (Compound B) were used. It was revealed that the solubility of the compound of the present invention, i.e., those obtained in Example 1 through Example 16, was greater than 10 mg/ml, while the solubility of Compound A and Compound B was 29 μg/ml and 18 μg/ml, respectively.

TEST EXAMPLE 2
Anticancer Activity Against Colon-26 (Mouse Colon Cancer) Cells Transplanted in Mice Colon-26 cells cultured in vitro were transplanted subcutaneously with an injection syringe in the right axillary region of Balb/c 5-week-old male mice (5×10$^5$ cells/animal). The mice were divided into groups of 6 animals/group when the tumor volume had reached about 120 mm$^3$ (Experiment 1) or about 100 mm$^3$ (Experiment 2). The test drug dissolved in 5% glucose solution was administered intravenously 5 times in total once daily at intervals of 4 days. The mice of control group were treated in the same manner with 5% glucose solution. The tumor volume was calculated according to the Equation 1 below on the basis of the major and minor axes of the tumor measured at a given interval with vernier calipers.

Equation 1:
$$\text{Tumor Volume} = \frac{1}{2} \times \text{major axis} \times (\text{minor axis})^2$$

The growth rate was then calculated according to the Equation 2 based on the tumor volume, which was then applied to the Equation 3 for the calculation of the growth inhibition rate in drug-treatment group relative to the control group.

Equation 2:
$$\text{Growth rate} = \frac{\text{tumor value at day } n}{\text{tumor volume at the initiation of administration}}$$

Equation 3:
$$\text{Growth inhibition rate (\%)} = 1 - \frac{\text{(growth rate in drug treatment group)}}{\text{growth rate in control group}} \times 100$$

The tumor growth inhibition rate and the number of survivals at day 21 after initiation of the administration are shown in Table 1.

TABLE 1

| Compound | Dose (mg/kg) | Tumor growth inhibition rate (%) | Number of Survival |
|---|---|---|---|
| Experiment 1 | | | |
| Control | | | 6/6 |
| Example 5 | 50 | 78.0 | 6/6 |
| | | 87.7 | 6/6 |
| Example 8 | 50 | 87.0 | 5/6 |
| | 75 | 95.9 | 5/6 |
| Example 9 | 50 | 80.8 | 6/6 |
| | 75 | 93.6 | 5/6 |
| Experiment 2 | | | |
| Control | | | 6/6 |
| Example 13 | 50 | 73.8 | 6/6 |
| | 75 | 92.6 | 6/6 |

TABLE 1-continued

| Compound | Dose (mg/kg) | Tumor growth inhibition rate (%) | Number of Survival |
|---|---|---|---|
| Example 14 | 50 | 78.6 | 6/6 |
|  | 75 | 84.1 | 6/6 |

The compounds of the present invention exhibited extremely potent tumor growth inhibition activity.

FORMULATION EXAMPLE 1

| Injection (in 1 ml) | |
|---|---|
| Compound of Example 9 | 10 mg |
| Mannitol | 50 mg |
| Injectable water | proper quantity to give 1 ml solution |

Process of Preparation

The compound of the present invention and mannitol are dissolved in the injectable water, filtered through membrane filter (0.22 μm) aseptically, filled in a vial and lyophilized to give an injection of extemporaneous dissolution type.

FORMULATION EXAMPLE 2

| Injection (in 1 ml) | |
|---|---|
| Compound of Example 9 | 10 mg |
| Maltose | 100 mg |
| Injectable water | proper quantity to give 1 ml solution |

Process of Preparation

The compound of the present invention and maltose are dissolved in the injectable water, filtered through membrane filter (0.22 μm) aseptically, filled in a vial and lyophilized to give an injection of extemporaneous dissolution type.

Industrial Applicability

The compound of the present invention is water-soluble and has potent anticancer activity with a low toxic potential. Accordingly, it is useful as an active ingredient of pharmaceutical compositions in the form of solutions especially injections which can be safely used on a long-term basis in the treatment of patients incapable of receiving oral administration for the treatment of various malignant tumors such as lung cancer, breast cancer, gastrointestinal cancer, prostate cancer, blood cancer, and the like.

What is claimed is:

1. A compound of the formula [I] or a salt thereof:

$$A\text{—}B\text{—}D\text{—}E\text{—} \qquad [I]$$

wherein

A is a 5- or 6-membered heteroaryl group having one or two nitrogen atoms as ring-composing members or its oxide;

B is an ethenylene group optionally substituted by cyano, bromo or $C_1$—$C_6$ alkyl;

D is a phenylene group optionally substituted by hydroxyl, halogen, amino, $C_1$—$C_6$ alkyl or $C_1$—$C_6$ alkoxy; and E is a group of the formula:

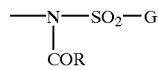

wherein G is a phenyl group optionally substituted by hydroxyl of $C_1$—$C_6$ alkoxy;

and R is a 5- or 6-membered heteroaryl group having one or two nitrogen atoms as ring-composing members or a 5- or 6-membered heteroarylmethyl group having one or two nitrogen atoms as ring-composing members, or a group of the formula:

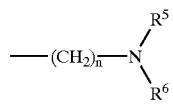

wherein n is an integer of 1 to 5; $R^5$ and $R^6$ are the same or different and independently selected from the group consisting of hydrogen, $C_1$—$C_6$ alkyl, or $R^5$ and $R^6$ taken together with the adjacent nitrogen atom may form a 5- to 7-membered cyclic amino group for —$NR^5(R^6)$ which may optionally be substituted by one or two substituents selected from the group consisting of alkyl, alkenyl, aryl, aralkyl, a 5- to 6-membered heteroaryl group having one to two nitrogen atoms and a 5- to 7-membered cyclic amino group.

2. The compound of the formula [I] according to claim 1 or a salt thereof, wherein A is 4-pyridyl or 1-oxido-4-pyridyl; B is ethenylene; D is optionally substituted phenylene; and E is the group of the formula:

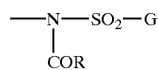

wherein R and G are the same as defined in claim 1.

3. The compound of the formula [I] according to claim 1 or a salt thereof, wherein A is 4-pyridyl or 1-oxido-4-pyridyl; B is ethenylene; D is optionally substituted phenylene; and E is the group of the formula:

wherein G is optionally substituted phenyl and R is the group of the formula:

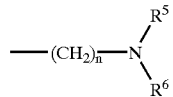

wherein n, $R^5$ and $R^6$ are the same as defined in claim 1.

4. The compound according to claim 3 or a salt thereof, wherein $R^5$ and $R^6$ are same or different and independently selected from the group consisting of hydrogen, $C_1$—$C_6$ alkyl; or $R^5$ and $R^6$ taken together with the adjacent nitrogen atom may form an optionally substituted 5- or 6-membered cyclic amino group for —$NR^5(R^6)$.

5. The compound of the formula [I] according to claim 1 or a salt thereof, wherein A is 4-pyridyl or 1-oxido-4-phridyl; B is ethenylene; D is phenylene; and E is the group of the formula:

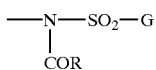

wherein G is optionally substituted phenyl; and R is optionally substituted 5- or 6-membered heteroaryl or heteroarylmethyl.

6. The salt according to claim 1 wherein the salt is hydrochloride.

7. A pharmaceutical composition comprising a compound of the formula [I] or a salt thereof mentioned in claim 1 as an active ingredient and a non-toxic carrier.

8. The pharmaceutical composition according to claim 7 which is in a form of injection.

9. A pharmaceutical composition for the treatment of a cancer comprising a compound of the formula [I] or a salt thereof mentioned in claim 1, as an active ingredient and a non-toxic carrier.

10. The anticancer agent according to claim 9 which is in a form of injection.

11. A method of treating cancer comprising administering to a subject in need of such treatment a therapeutically effective amount of the pharmaceutical composition comprising a compound of the formula [I] or a salt thereof mentioned in claim 1.

* * * * *